(12) United States Patent
Haynes et al.

(10) Patent No.: US 7,915,446 B2
(45) Date of Patent: Mar. 29, 2011

(54) CATALYST AND PROCESS FOR THE PRODUCTION OF ACETIC ACID

(75) Inventors: Anthony Haynes, Sheffield (GB); David John Law, East Yorkshire (GB); Andrew Miller, Hull (GB); George Ernest Morris, East Yorkshire (GB); Marc John Payne, Oxfordshire (GB); John Glenn Sunley, East Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 475 days.

(21) Appl. No.: 10/563,920

(22) PCT Filed: Jun. 23, 2004

(86) PCT No.: PCT/GB2004/002686
§ 371 (c)(1),
(2), (4) Date: Jan. 10, 2006

(87) PCT Pub. No.: WO2005/009939
PCT Pub. Date: Feb. 3, 2005

(65) Prior Publication Data
US 2006/0155144 A1     Jul. 13, 2006

(30) Foreign Application Priority Data
Jul. 17, 2003  (GB) .................................. 0316756.6

(51) Int. Cl.
*C07C 51/16* (2006.01)
(52) U.S. Cl. ...................................... 562/525
(58) Field of Classification Search .................... 560/232
See application file for complete search history.

(56) References Cited

U.S. PATENT DOCUMENTS

| | | | | |
|---|---|---|---|---|
| 4,469,886 A * | 9/1984 | Pesa et al. | ...................... | 562/522 |
| 4,629,809 A * | 12/1986 | Vanderpool et al. | .......... | 562/519 |
| 5,166,419 A * | 11/1992 | Tokumoto et al. | ............ | 562/406 |
| 5,281,751 A | 1/1994 | Schreck | | |
| 5,625,094 A | 4/1997 | Nobel et al. | | |
| 5,710,325 A * | 1/1998 | Bruner et al. | .................. | 562/517 |
| 5,831,120 A * | 11/1998 | Watson et al. | ................ | 562/519 |
| 6,255,527 B1 * | 7/2001 | Muskett | ........................ | 562/519 |
| 6,521,783 B1 * | 2/2003 | Wegman et al. | .............. | 560/232 |

FOREIGN PATENT DOCUMENTS

| | | |
|---|---|---|
| EP | 0 643 034 A1 | 3/1995 |
| EP | 0 752 406 A1 | 1/1997 |
| EP | 0752406 A1 * | 8/1997 |
| EP | 0 849 250 A1 | 6/1998 |
| EP | 1 099 680 A2 | 5/2001 |
| EP | 1 099 681 A2 | 5/2001 |
| EP | 1 099 680 A3 | 1/2003 |
| EP | 1 099 681 A3 | 1/2003 |
| GB | 1 276 326 | 6/1972 |
| WO | WO 03/104179 A1 | 12/2003 |

\* cited by examiner

*Primary Examiner* — Jessica L Ward
*Assistant Examiner* — Yoshitoshi Takeuchi
(74) *Attorney, Agent, or Firm* — Nixon & Vanderhye

(57) ABSTRACT

A catalyst and process for the production of acetic acid by the carbonylation of methanol and/or a reactive derivative thereof. The catalyst system comprises an iridium carbonylation catalyst, methyl iodide co-catalyst, optionally at least one of ruthenium, osmium, rhenium, zinc, gallium, tungsten, cadmium, mercury and indium and at least one non-hydrohalogenoic acid promoter. The non-hydrohalogenoic acid may be an oxoacid, a superacid and/or a heteropolyacid.

23 Claims, No Drawings

CATALYST AND PROCESS FOR THE PRODUCTION OF ACETIC ACID

This application is the U.S. National Phase of International Application PCT/GB2004/002686, filed 23 Jun. 2004, which designated the U.S. PCT/GB2004/002686 claims priority to British Application No. 0316756.6 filed 17 Jul. 2003. The entire content of these applications are incorporated herein by reference.

The present invention relates to a process for the production of acetic acid and in particular, to a process for the production of acetic acid by carbonylation in the presence of an iridium catalyst and methyl iodide co-catalyst.

The production of acetic acid by the carbonylation of methanol in the presence of an iridium catalyst is known and is described, for example in, EP-A-0643034 and EP-A-0752406.

EP-A-0643034 describes a process for the production of acetic acid by carbonylation of methanol or a reactive derivative thereof which process comprises contacting methanol or a reactive derivative thereof with carbon monoxide in a liquid reaction composition in a carbonylation reactor characterised in that the liquid composition comprises (a) acetic acid, (b) an iridium catalyst, (c) methyl iodide, (d) at least a finite quantity of water, (e) methyl acetate and (f) as promoter, at least one of ruthenium and osmium.

EP-A-0752406 describes a process for the production of acetic acid comprising (1) continuously feeding methanol and/or a reactive derivative thereof and carbon monoxide to a carbonylation reactor which contains a liquid reaction composition comprising an iridium carbonylation catalyst, methyl iodide co-catalyst, a finite concentration of water, acetic acid, methyl acetate and at least one promoter; (2) contacting the methanol and/or reactive derivative thereof with the carbon monoxide in the liquid reaction composition to produce acetic acid; and (3) recovering acetic acid from the liquid reaction composition characterised in that there is continuously maintained in the liquid reaction composition throughout the course of the reaction (a) water at a concentration of no greater than 6.5% by weight, (b) methyl acetate at a concentration in the range 1 to 35% by weight and (c) methyl iodide at a concentration in the range 4 to 20% by weight.

It has now been surprisingly found that by using a non-hydrohalogenoic acid in an iridium-catalysed carbonylation process for the production of acetic acid improved carbonylation rates may be achieved.

In the iridium-catalysed carbonylation of methanol (or reactive derivative thereof) hydriodic acid is generated and consumed via the following reaction mechanisms acyl iodide+water→acetic acid+hydriodic acid hydriodic acid+methyl acetate→methyl iodide+acetic acid As the concentration of hydriodic acid is increased the rate of carbonylation is found to decrease. It is therefore surprising that the concentration of protons ($H^+$) in the carbonylation system can be increased without having a detrimental effect on the carbonylation rate.

Thus, according to the present invention there is provided a catalyst system for the production of acetic acid which catalyst system comprises an iridium carbonylation catalyst, methyl iodide co-catalyst, optionally at least one of ruthenium, osmium, rhenium, zinc, gallium, tungsten, cadmium, mercury and indium and at least one non-hydrohalogenoic acid promoter.

The present invention also provides a process for the production of acetic acid by reacting carbon monoxide with methanol and/or a reactive derivative thereof in a liquid reaction composition comprising methyl acetate, a finite concentration of water, acetic acid and a catalyst system comprising an iridium carbonylation catalyst, methyl iodide co-catalyst, optionally at least one of ruthenium, osmium, rhenium, zinc, gallium, tungsten, cadmium, mercury and indium and at least one non-hydrohalogenoic acid promoter.

The present invention further provides for the use of a catalyst system for the production of acetic acid which catalyst system comprises an iridium carbonylation catalyst, methyl iodide co-catalyst, optionally at least one of ruthenium, osmium, rhenium, zinc, gallium, tungsten, cadmium, mercury and indium and at least one non-hydrohalogenoic acid promoter.

The non-hydrohalogenoic acid for use in the process present invention may suitably be at least one of an oxoacid, a superacid and a heteropolyacid. Mixtures of non-hydrohalogenoic acids of the same or different type may be used such as mixtures of at least two different oxoacids or at least two different superacids or at least two different heteropolyacids or a mixture of at least one oxoacid and/or at least one superacid and/or at least one heteropolyacid. It will be understood by the skilled person that an acid may be both of the oxoacid and a superacid type.

Oxoacids are compounds with X—OH groups of the type $H_nXO_m$ wherein X is a non-metal or metal and n and m are integers. Examples of common oxoacids are $H_3PO_4$, $H_2SO_4$, $HNO_3$ and $HClO_4$ Suitable oxoacids for use in the process of the present invention include the oxoacids of the elements of Groups 13 to 17 of the Periodic Table.

Suitable oxoacids of the elements of Group 13 include the oxoacids of boron such as $H_3BO_3$. Group 14 oxoacids include those of germanium such as $H_4GeO_4$. Group 15 oxoacids include the oxoacids of nitrogen, phosphorus and arsenic. Suitable nitrogen-containing oxoacids include $HNO_3$ and $HNO_2$. Examples of phosphorus-containing oxoacids include $H_3PO_4$, $H_3PO_3$ and $H_3PO_2$. Examples of arsenic-containing oxoacids include $H_3AsO_3$. Group 16 oxoacids include the oxoacids of sulphur such as $H_2SO_4$, $H_2SO_3$, triflic acid, p-toluenesulphonic acid, selenium, for example $H_2SeO_3$ and $H_2SeO_4$ and tellurium such as $H_6TeO_6$. Group 17 oxoacids may be oxoacids of bromine, iodine and chlorine such as HBrO, HClO, $H_5IO_6$, $HClO_2$ and $HClO_4$.

Preferred oxoacids are $H_2SO_4$, $HNO_3$ and $H_3PO_4$ or mixtures thereof.

Acidity can be measured in a wide variety of solvents. Typically the acidity of a substance is measured in water and the hydrogen ion concentration generated by the substance therein is often given in terms of the pH scale. Solutions of a substance having a pH lower than 7.0 are acidic; those of higher pH are alkaline. However, the concepts of hydrogen ion concentration and pH are meaningful only for dilute aqueous solutions of acids. Thus, a widely used means for determining acidity in other media and at high concentrations is the Hammett acidity function $H_0$. The acidity function, $H_0$, is defined as

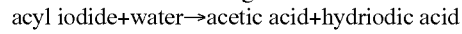

$$H_0 = pK_{BH+} - \log [BH^+]/[B]$$

where

[B] is concentration of a weak base (indicator)

[$H^+$] is concentration of the conjugate acid of the weak base $pK_{BH+}$ is pK of indicator in water The $H_0$ value of an acidic substance is measured using indicators that are weak bases (B) such as o-nitroaniline or 2,4-dinitroaniline. The weak base is (partly) converted in the acidic substance to the conjugate acid of the base ($BH^+$). The value of [$BH^+$]/[B] is typically measured by spectrophotometric means. By using the known pK in water for the base, $H_0$ can then be calculated for the acidic substance.

Acidic substances with $-H_0$ values above about 12 are referred to as superacids. Superacids are upward of $10^6$ times as strong as a 1 molar aqueous solution of a strong acid. Acids with a $-H_0$ of greater than 12.1 (measured as the pure acid), are suitable for use in the process of the present invention.

The superacids for use in the process of the present invention have non-coordinating anions by which is meant that little or no covalent interaction between the anion and iridium.

Suitable superacids for use in the process of the present invention include acids which have the following anions $BF_4^-$, $PF_6^-$, $(CF_3SO_2)_2N^-$, $CBH_6Br_6^-$, $CF_3SO_3^-$, $SbF_6^-$, $FSO_3^-$ or mixtures thereof.

Specific examples of suitable superacids include $HBF_4$, $HPF_6$, $(CF_3SO_2)_2NH$ and $HCBH_6Br_6$.

The term "heteropolyacid" as used herein and throughout the specification means the free acid and does not include the associated metal salts thereof. The heteropolyacid anion may comprise from two to eighteen oxygen-linked polyvalent metal atoms, which are generally known as the "peripheral" atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for instance, cupric ions; divalent beryllium, zinc, cobalt or nickel ions; trivalent boron, aluminum, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters".

Heteropolyacids usually have a high molecular weight, for example, in the range from 700-8500 and include dimeric complexes. They have a relatively high solubility in polar solvents such as water or other oxygenated solvents, especially if they are free acids. Suitably, the heteropolyacid may have molybdenum and/or tungsten as peripheral atoms. Specific examples of heteropolyacids that may be used in the process of the present invention include:
12-tungstophosphoric acid—$H_3[PW_{12}O_{40}].xH_2O$
12-molybdophosphoric acid—$H_3[PMo_{12}O_{40}].xH_2O$
12-tungstosilicic acid—$H_4[SiW_{12}O_{40}].xH_2O$
12-molybdosilicic acid—$H_4[SiMo_{12}O_{40}].xH_2O$ The non-hydrohalogenoic acid for use in the process of the present invention may be introduced directly into the reactor, together with or separately from a reactant feed stream. The non-hydrohalogenoic acid may be used in the form of an aqueous solution of the acid.

The amount of the non-hydrohalogenoic acid to be used in the process of the present invention should be sufficient to provide a promotional effect on the carbonylation rate. The exact amount will depend on the specific non-hydrohalogenoic used and, in particular, on the nature and concentration of the anion of the acid. Without wishing to be bound by any theory, it is believed that certain anions, such as those of oxoacids, may co-ordinate to the iridium metal, and thus, if the concentration of these oxoanions is too high, a detrimental effect of the carbonylation rate may ensue. However, if the anion is non-coordinating to the iridium metal, higher concentrations of the acid may be employed.

Suitably, the amount of a superacid which may be added to the liquid reaction composition is such that the molar ratio of the anion to iridium is in the range [greater than 0 to 2.5]:1, preferably, in the range [greater than 0 to 1]:1, especially, in the range [0.05 to 0.5]:1.

Typically, the amount of oxoacid which may be added to the liquid reaction composition is such that the molar ratio of anion to iridium is in the range [greater than 0 to 0.4]:1. Where the anion is $SO_4^{2-}$, $NO_3^-$ or $PO_4^{3-}$, derived from sulphuric, nitric and phosphoric acids respectively, the molar ratio of anion to iridium is preferably in the range [greater than 0 to 0.4]:1, suitably [greater than 0 to 0.35]:1, such as in the range [0.05 to 0.3]:1.

Suitably, the amount of a heteropolyacid which may be added to the liquid reaction composition is such that the molar ratio of the anion to iridium is in the range [greater than 0 to 5]:1, preferably, in the range [greater than 1 to 4]:1, especially, in the range [1.5 to 3.5]:1.

The iridium catalyst in the liquid reaction composition may comprise any iridium-containing compound which is soluble in the liquid reaction composition. The iridium catalyst may be added to the liquid reaction composition in any suitable form which dissolves in the liquid reaction composition or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentration of the iridium catalyst in the liquid reaction composition is in the range 100 to 6000 ppm by weight of iridium.

Optionally, the liquid reaction composition may also comprise one or more of ruthenium, osmium, rhenium, zinc, gallium, tungsten, cadmium, mercury and indium, more preferably ruthenium and osmium. The ruthenium, osmium, rhenium, zinc, gallium, tungsten, cadmium, mercury and indium may be used in any suitable metal-containing compound which is soluble in the liquid reaction composition. The ruthenium, osmium, rhenium, zinc, gallium, tungsten, cadmium, mercury and indium may be added to the liquid reaction composition for the carbonylation reaction in any suitable form which dissolves in the liquid reaction composition or is convertible to soluble form.

Examples of suitable ruthenium-containing compounds which may be used as include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]$—$H+$, $[Ru(CO)_2I_2]_n$, $[Ru(CO)_4I_2]$, $[Ru(CO)_3I_2]_2$, tetra(aceto)chlororuthenium(II, III), ruthenium (III) acetate, ruthenium (III) propionate, ruthenium (III) butyrate, ruthenium pentacarbonyl, triruthenium dodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium (II), tetrachlorobis(benzene)diruthenium(II), dichloro(cyclooocta-1,5diene) ruthenium (II) polymer and tris(acetylacetonate)ruthenium (III).

Examples of suitable osmium-containing compounds which may be used include osmium (III) chloride hydrate and anhydrous, osmium metal, osmium tetraoxide, triosmium-dodecacarbonyl, $[Os(CO)_4I_2]$, $[Os(CO)_3I_2]_2$, $[Os(CO)_3I_3]$—H+, pentachloro-μ-nitrodiosmium and mixed osmium halocarbonyls such as tricarbonyldichloroosmium (II) dimer and other organoosmium complexes.

Examples of suitable rhenium-containing compounds which may be used include $Re_2(CO)_{10}$, $Re(CO)_5Cl$, $Re(CO)_5Br$, $Re(CO)_5I$, $ReCl_3.xH_2O$, $[Re(CO)_4I]_2$, $Re(CO)_4I_2]^-H^+$ and $ReCl_5.yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used include $Hg(OAC)_2$, $HgI_2$, $HgBr_2$, $HgCl_2$, $Hg_2I_2$, and $Hg_2Cl_2$.

Examples of suitable zinc-containing compounds which may be used include $Zn(OAc)_2$, $Zn(OH)_2$, $ZnI_2$, $ZnBr_2$, $ZnCl_2$, and zinc acetylacetonate.

Examples of suitable gallium-containing compounds which may be used include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used include indium acetylacetonate, indium acetate, $InCl_3$, $InBr_3$, $InI_3$, $InI$ and $In(OH)_3$.

Examples of suitable tungsten-containing compounds which may be used include $W(CO)_6$, $WCl_4$, $WCl_6$, $WBr_5$, $WI_2$, $C_9H_{12}W(CO)_3$ and any tungsten chloro-, bromo- or iodo-carbonyl compound.

Where ruthenium, osmium, rhenium, zinc, gallium, tungsten, cadmium, mercury and/or indium is used, it is preferably present in an effective amount up to the limit of its solubility in the liquid reaction composition and/or any liquid process streams recycled to the carbonylation reactor from the acetic acid recovery stage. The ruthenium, osmium, rhenium, zinc, gallium, tungsten, cadmium, mercury and/or indium is suitably present in the liquid reaction composition at a molar ratio of metal to iridium of [1 to 15]:1, preferably [2 to 10]:1, more preferably [4 to 10]:1. A suitable ruthenium, osmium or rhenium, zinc, gallium, tungsten, cadmium, mercury and/or indium concentration is less than 8000 ppm, such as 400 to 7000 ppm.

Preferably, the iridium- and any ruthenium, osmium, rhenium, zinc, gallium, tungsten, cadmium, mercury and indium-containing compounds are free of impurities which provide or generate in situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen containing compounds or ligands which may quaternise in situ; should be kept to a minimum in the liquid reaction composition as these will have an adverse effect on the reaction by generating $I^-$ in the liquid reaction composition which has an adverse effect on the reaction rate. Some corrosion metal contaminants such as for example, molybdenum have been found to be less susceptible to the generation of $I^-$. Corrosion metals which have an adverse affect on the reaction rate may be minimised by using suitable corrosion resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130. Preferably, ionic contaminants are kept below a concentration at which they would generate 500 ppm $I^-$, preferably less than 250 ppm $I^-$ in the liquid reaction composition.

In the process of the present invention, the concentration of methyl iodide co-catalyst in the liquid reaction composition is preferably in the range 5 to 16% by weight.

In the process of the present invention, suitable reactive derivatives of methanol include methyl acetate, dimethyl ether and methyl iodide. A mixture of methanol and reactive derivatives thereof may be used as reactants in the process of the present invention. Water is required as co-reactant for ether or ester reactants. Preferably, methanol and/or methyl acetate are used as reactants.

At least some of the methanol and/or reactive derivative thereof will be converted to, and hence present as, methyl acetate in the liquid reaction composition by reaction with the carboxylic acid product or solvent. Preferably, the concentration of methyl acetate in the liquid reaction composition is in the range 1 to 70% by weight, more preferably 2 to 50% by weight, most preferably 3 to 35% by weight Water may be formed in-situ in the liquid reaction composition, for example, by the esterification reaction between methanol reactant and acetic acid product. Small amounts of water may also be produced by hydrogenation of methanol to produce methane and water. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. The water concentration in the liquid reaction composition is suitably in the range 1-15 wt %, such as 1-10 wt %, preferably in the range 1-6.5 wt %.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide feed and generated in-situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the carbonylation reactor is preferably less than $1\times10^5$ $N/m^2$ partial pressure, more preferably less than $5\times10^4$ $N/m^2$ and yet more preferably less than $3\times10^4$ $N/m^2$. The partial pressure of carbon monoxide in the reactor is suitably in the range $1\times10^5$ $N/m^2$ to $7\times10^6$ $N/m^2$, preferably $1\times10^5$ $N/m^2$ to $3.5\times10^6$ $N/m^2$, more preferably $1\times10^5$ $N/m^2$ to $1.5\times10^6$ $N/m^2$.

The total pressure of the carbonylation reaction is suitably in the range $1\times10^6$ $N/m^2$ to $2\times10^7$ $N/m^2$, preferably $1.5\times10^6$ $N/m^2$ to $1\times10^7$ $N/m^2$, more preferably $1.5\times10^6$ $N/m^2$ to $5\times10^6$ $N/m^2$.

The temperature of the carbonylation reaction is suitably in the range 100 to 300° C., preferably in the range 150 to 220° C.

The process of the present invention may be performed as a batch or as a continuous process, but is preferably performed as a continuous process.

The acetic acid product may be recovered from the liquid reaction composition by withdrawing vapour and/or liquid from the carbonylation reactor and recovering acetic acid from the withdrawn material. Preferably, acetic acid is recovered from the liquid reaction composition by continuously withdrawing liquid reaction composition from the carbonylation reactor and recovering acetic acid from the withdrawn liquid reaction composition by one or more flash and/or fractional distillation stages in which the acetic acid is separated from the other components of the liquid reaction composition such as iridium catalyst, methyl iodide co-catalyst, methyl acetate, unreacted methanol, water and acetic acid solvent which may be recycled to the reactor to maintain their concentrations in the liquid reaction composition. To maintain stability of the iridium catalyst during the acetic acid product recovery stage, water in process streams containing iridium carbonylation catalyst for recycle to the carbonylation reactor should be maintained at a concentration of at least 0.5% by weight.

The process of the present invention may be performed a using carbonylation reaction conditions known in the art, for example as described in EP-A-0786447, EP-A-0643034, EP-A-0752406 and EP-A-0749948, the contents of which are hereby incorporated by reference.

The invention will now be illustrated by way of example only and with reference to the following examples:

General Reaction Method

All experiments were performed in a 300 cm$^3$ zirconium autoclave equipped with a stirrer, liquid injection facility, ballast vessel and gas feed lines. Ruthenium acetate solution (when used, 5.08 wt % ruthenium metal, 71.3 wt % acetic acid and 17.8 wt % water), an aqueous solution of a non-hydrohalogenoic acid (when used) and part of the acetic acid charge (10 g) were weighed into the autoclave base. The head of the autoclave was placed on the base and sealed before transferring the assembled unit to a blast cell. An electrical radiant heater and thermocouple were placed on the autoclave assembly before connecting to the gas and liquid feed lines, water cooling hoses and overhead stirrer. The gas and liquid feed inlet valves were opened and the assembly pressure tested with nitrogen (32 N/m$^2$). The unit was flushed with nitrogen (1×20 N/m$^2$ pressure and vent cycle) followed by carbon monoxide (3×5 bar g pressure and vent cycles). The autoclave was opened to vent. Methyl iodide (13.33 g) followed by a mixture of water (approximately 13.15 g), acetic acid (approximately 42.66 g) and methyl acetate (approximately 48.0 g) was added via a funnel before the autoclave was resealed. 6.3 g iridium acetate solution (5.25 wt % iridium metal, 71.9 Wt/o acetic acid and 18.0 wt % water) was placed into the catalyst injector and washed in with the remaining acetic acid (approximately 8.7 g). Reactor charge compositions were adjusted so the water, methyl iodide, methyl acetate and acetic acid levels were identical after catalyst injection for each reaction. The autoclave stirrer was switched on (1500 rpm) before pressurising with carbon monoxide (8 N/m$^2$). The assembly was heated to reaction temperature (190° C.). Once the temperature had stabilised the pressure in the autoclave was adjusted to the desired initial pressure as was the catalyst injector. The ballast vessel was charged with carbon monoxide before injecting the catalyst solution with an over-pressure of carbon monoxide to bring the autoclave pressure to 28 bar g. After injection the autoclave pressure was kept constant at 28 N/m$^2$ by feeding carbon monoxide from the ballast vessel on demand. The temperature in the autoclave was kept constant by controlling the flow of cooling water. The reaction rate was monitored by the drop in carbon monoxide pressure from the ballast vessel which was initially pressurised to approximately N/m$^2$. On completion of the run the ballast vessel was isolated, the heater switched off and the autoclave cooled to below 30° C. Once below 30° C. a gas sample could be taken from the head-space, if desired, before removing the autoclave from the blast cell and discharging. Liquid components were analysed by known, established gas chromatography methods. Detected components were quantified by integration of the component peaks relative to an external standard and expressed as parts per million (ppm) by mass. The major component in each batch carbonylation was acetic acid.

The rate of gas uptake at a certain point in a reaction run was used to calculate the carbonylation rate, as number of moles of reactant consumed per litre of cold degassed reactor composition per hour (mol.dm$^{-3}$.hr$^{-1}$) at a particular reactor composition (total reactor composition based on a cold degassed volume).

Methyl acetate concentration was calculated during the course of the reaction from the starting composition, assuming that one mole of methyl acetate was consumed from every mole of carbon monoxide that was consumed. No allowance was made for the organic components in the autoclave headspace.

EXAMPLES

Experiment A

A baseline experiment was performed with the autoclave charged with methyl acetate (48.0 g), acetic acid (55.63 g), ruthenium acetate solution (6.87 g), water (13.16 g) and methyl iodide (13.33 g). The catalyst charge consisted of an iridium solution (6.30 g) with acetic acid (5.73 g). The ratio of iridium to ruthenium was 1:2. The rate of reaction at a calculated reactor composition of 12% w/w methyl acetate is shown in Table 1.

Example 1

Experiment A was repeated except that the autoclave was also charged with 98% H$_2$SO$_4$ solution (0.0172 g). The rate of reaction at a calculated reactor composition of 12% w/w methyl acetate is shown in Table 1.

Experiment 2

Experiment A was repeated except that the autoclave was also charged with 98% H$_2$SO$_4$ solution (0.08 g). The rate of reaction at a calculated reactor composition of 12% w/w methyl acetate is shown in Table 1.

Experiment 3

Experiment A was repeated except that the autoclave was also charged with 98% H$_2$SO$_4$ solution (0.345 g). The rate of reaction at a calculated reactor composition of 12% w/w methyl acetate is shown in Table 1.

TABLE 1

| Example/Experiment | Oxoacid | Ir/Ru/Oxoacid Molar Ratio | Rate at 12% MeOAc (mol · dm$^{-3}$ · hr$^{-1}$) |
|---|---|---|---|
| A | None | 1:2:0 | 18.3 |
| 1 | H$_2$SO$_4$ | 1:2:0.1 | 20.2 |
| 2 | H$_2$SO$_4$ | 1:2:0.5 | 17.8 |
| 3 | H$_2$SO$_4$ | 1:2:2 | 8.8 |

From an inspection of Table 1, it can be seen that the presence of a non-hydrohalogenoic acid (sulphuric acid) in a molar ratio of sulphate ions to iridium in a promotional amount provides an increased carbonylation rate compared to Experiments in which no non-hydrohalogenoic acid was present or where a high concentration of sulphate anion was present:

Experiment B

A baseline experiment was performed with the autoclave charged with methyl acetate (48.0 g), acetic acid (57.58 g), water (14.37 g) and methyl iodide (13.33 g). The catalyst charge consisted of an iridium solution (6.30 g) with acetic acid (8.70 g). The rate of reaction at a calculated reactor composition of 12% w/w methyl acetate is shown in Table 2.

Experiment 4

Experiment B was repeated except that the autoclave was also charged with 85% $H_3PO_4$ solution (0.034 g). The rate of reaction at a calculated reactor composition of 12% w/w methyl acetate is shown in Table 2.

TABLE 2

| Example/Experiment | Oxoacid | Ir/Oxoacid Molar Ratio | Rate at 12% MeOAc $(mol \cdot dm^{-3} \cdot hr^{-1})$ |
|---|---|---|---|
| B | None | 1:0 | 8.5 |
| 4 | $H_3PO_4$ | 1:0.17 | 10.2 |

From an inspection of Table 1, it can be seen that the presence of orthophosphoric acid provides an increased carbonylation rate compared to Experiment B in which no non-hydrohalogenoic acid was present.

Experiment C

A baseline experiment was performed with the autoclave charged with methyl acetate (48.0 g), acetic acid (55.63 g), ruthenium acetate solution (6.87 g), water (13.16 g) and methyl iodide (13.33 g). The catalyst charge consisted of an iridium solution (6.30 g) with acetic acid (5.73 g). The ratio of iridium to ruthenium was 1:2. The rate of reaction at a calculated reactor composition of 12% w/w methyl acetate is shown in Table 3.

Experiment D

A baseline experiment was performed with the autoclave charged with methyl acetate (48.0 g), acetic acid (42.83 g), ruthenium acetate solution (20.54 g), water (10.71 g) and methyl iodide (13.33 g). The catalyst solution consisted of an iridium solution (6.30 g) with acetic acid (8.70 g). The ratio of iridium to ruthenium was 1:6. The rate of reaction at a calculated reactor composition of 12% w/w methyl acetate is shown in Table 3.

Experiment E

A baseline experiment was performed with the autoclave charged with methyl acetate (48.0 g), acetic acid (42.83 g), water (10.71 g) and methyl iodide (13.33 g). The catalyst solution consisted of an iridium solution (6.30 g) with acetic acid (8.70 g). The rate of reaction at a calculated reactor composition of 12% w/w methyl acetate is shown in Table 3.

Example 5

Experiment C was repeated except that the autoclave was also charged with 60% $HPF_6$ solution (0.027 g). The rate of reaction at a calculated reactor composition of 12% w/w methyl acetate is shown in Table 3.

Example 6

Experiment C was repeated except that the autoclave was also charged with 60% $HPF_6$ solution (0.042 g). The rate of reaction at a calculated reactor composition of 12% w/w methyl acetate is shown in Table 3.

Example 7

Experiment C was repeated except that the autoclave was also charged with 60% $HPF_6$ solution (0.084 g). The rate of reaction at a calculated reactor composition of 12% w/w methyl acetate is shown in Table 3.

Example 8

Experiment C was repeated except that the autoclave was also charged with 60% $HPF_6$ solution (0.43 g). The rate of reaction at a calculated reactor composition of 12% w/w methyl acetate is shown in Table 3.

Example 9

Experiment C was repeated except that the autoclave was also charged with 60% $HPF_6$ solution (0.9 g). The rate of reaction at a calculated reactor composition of 12% w/w methyl acetate is shown in Table 3.

Example 10

Experiment C was repeated except that the autoclave was also charged with 48% $HBF_4$ solution (0.17 g). The rate of reaction at a calculated reactor composition of 12% w/w methyl acetate is shown in Table 3.

Example 11

Experiment D was repeated except that the autoclave was also charged with 60% $HPF_6$ solution (0.05 g). The rate of reaction at a calculated reactor composition of 12% w/w methyl acetate is shown in Table 3.

Example 12

Experiment E was repeated except that the autoclave was also charged with 48% $HPF_6$ solution (0.17 g). The rate of reaction at a calculated reactor composition of 12% w/w methyl acetate is shown in Table 3.

Example 13

Experiment E was repeated except that the autoclave was also charged with $(CF_3SO_2)_2NH$ (0.24 g). The rate of reaction at a calculated reactor composition of 12% w/w methyl acetate is shown in Table 3.

TABLE 3

| Experiment | Acid | Ir/Ru/Acid Molar Ratio | Rate at 12% MeOAc $(mol \cdot dm^{-3} \cdot hr^{-1})$ |
|---|---|---|---|
| C | None | 1:2:0 | 18.3 |
| 5 | $HPF_6$ | 1:2:0.1 | 20.3 |
| 6 | $HPF_6$ | 1:2:0.1 | 20.3 |
| 7 | $HPF_6$ | 1:2:0.2 | 19.2 |
| 8 | $HPF_6$ | 1:2:1.0 | 19.8 |
| 9 | $HPF_6$ | 1:2:2.2 | 19.8 |
| 10 | $HBF_4$ | 1:2:0.5 | 20.8 |

TABLE 3-continued

| Experiment | Acid | Ir/Ru/Acid Molar Ratio | Rate at 12% MeOAc (mol·dm⁻³·hr⁻¹) |
|---|---|---|---|
| D | None | 1:6:0.0 | 27.3 |
| 11 | HPF$_6$ | 1:6:0.1 | 29.1 |
| E | None | 1:0:0 | 8.1 |
| 12 | HBF$_4$ | 1:0:0.5 | 10.5 |
| 13 | (CF$_3$SO$_2$)$_2$NH | 1:0:0.5 | 11.2 |

From an inspection of Table 3, it can clearly be seen from a comparison of Experiments C and D (where no non-hydrohalogenoic acid was present) with Examples 5 to 9 and 11 (where hexafluorophosphoric acid was used) that an increase in carbonylation rate was achieved in Examples 5 to 9 and 11.

A comparison of Experiment C with Example 10 (where tetrafluoroboric acid was present) shows that the addition of an acid according to the present invention provides an increase in carbonylation rate similar to that observed in Examples 5 to 9.

A comparison of Experiment E with Examples 12 and 13 shows that the addition of acids according to the present invention (tetrafluoroboric acid; (CF$_3$SO$_2$)$_2$NH) provide an increase in carbonylation rate in the absence of a ruthenium promoter.

Experiment F

A baseline experiment was performed with the autoclave charged with methyl acetate (48.0 g), acetic acid (57.58 g), water (14.37 g) and methyl iodide (13.33 g). The catalyst solution consisted of an iridium solution (6.60 g) with acetic acid (8.70 g). The rate of reaction at a calculated reactor composition of 12% w/w methyl acetate is shown in Table 4.

Example 14

Experiment F was repeated except that the autoclave was also charged with H$_3$[PW$_{12}$O$_{40}$].xH$_2$O solid (5.835 g) and a reduced amount of acetic acid (53.38 g). The rate of reaction at a calculated reactor composition of 12% w/w methyl acetate is shown in Table 4.

Example 15

Experiment F was repeated except that the autoclave was also charged with H$_3$[PW$_{12}$O$_{40}$].xH$_2$O solid (11.68 g) and a reduced amount of acetic acid (47.31 g). The rate of reaction at a calculated reactor composition of 12% w/w methyl acetate is shown in Table 4.

Example 16

Experiment F was repeated except that the autoclave was also charged with H$_3$[PW$_{12}$O$_{40}$].xH$_2$O solid (17.47 g) and a reduced amount of acetic acid (41.4 g). The rate of reaction at a calculated reactor composition of 12% w/w methyl acetate is shown in Table 4.

Example 17

Experiment F was repeated except that the autoclave was also charged with H$_4$[SiW$_{12}$O$_{40}$].xH$_2$O solid (5.84 g) and a reduced amount of acetic acid (53.38 g). The rate of reaction at a calculated reactor composition of 12% w/w methyl acetate is shown in Table 4.

Example 18

Experiment F was repeated except that the autoclave was also charged with H$_4$[SiW$_{12}$O$_{40}$].xH$_2$O solid (11.72 g) and a reduced amount of acetic acid (47.38 g). The rate of reaction at a calculated reactor composition of 12% w/w methyl acetate is shown in Table 4.

TABLE 4

| Example/ Experiment | HeteroPolyAcid (HPA) | Ir/HPA anion Molar Ratio | Rate at 12% MeOAc (mol·dm⁻³·hr⁻¹) |
|---|---|---|---|
| F | None | 1:0 | 9.8 |
| 14 | H$_3$[PW$_{12}$O$_{40}$].xH$_2$O | 1:1 | 13.9 |
| 15 | H$_3$[PW$_{12}$O$_{40}$].xH$_2$O | 1:2 | 16.3 |
| 16 | H$_3$[PW$_{12}$O$_{40}$].xH$_2$O | 1:3 | 16.7 |
| 17 | H$_4$[SiW$_{12}$O$_{40}$].xH$_2$O | 1:1 | 12.4 |
| 18 | H$_4$[SiW$_{12}$O$_{40}$].xH$_2$O | 1:2 | 14.2 |

From Table 4 it can be seen that the presence of a heteropolyacid in Examples 14 18 provides an increased carbonylation rate compared to Experiment F where no heteropolyacid is present.

Experiment G

A baseline experiment was performed with the autoclave charged with methyl acetate (48.0 g), acetic acid (52.64 g), water (13.16 g), methyl iodide (13.33 g) and ruthenium solution (6.87 g). The catalyst solution consisted of an iridium solution (6.30 g) with acetic acid (8.70 g). The rate of reaction at a calculated reactor composition of 12% w/w methyl acetate is shown in Table 5.

Example 19

Experiment G was repeated except that the autoclave was also charged with H$_3$[PW$_{12}$O$_{40}$].xH$_2$O solid (11.67 g), ruthenium acetate (6.87 g) and a reduced amount of acetic acid (32.53 g). The rate of reaction at a calculated reactor composition of 12% w/w methyl acetate is shown in Table 4.

Example 20

Experiment G was repeated except that the autoclave was also charged with H$_3$[PW$_{12}$O$_{40}$].xH$_2$O solid (5.95 g), indium acetate (0.534 g) and a reduced amount of acetic acid (41.4 g). The rate of reaction at a calculated reactor composition of 12% w/w methyl acetate is shown in Table 4.

TABLE 5

| Example/ Experiment | Promoter Metal (M) | HetroPolyAcid (HPA) | Ir/M/ HPA anion Molar Ratio | Rate at 12% MeOAc (mol·dm⁻³·hr⁻¹) |
|---|---|---|---|---|
| G | Ruthenium | None | 1:2:0 | 21.0 |
| 19 | Ruthenium | H$_3$[PW$_{12}$O$_{40}$].xH$_2$O | 1:2:2 | 25.9 |
| 20 | Indium | H$_3$[PW$_{12}$O$_{40}$].xH$_2$O | 1:1:1 | 15.5 |

From a comparison of Experiment G and Example 19 in Table 5 and also from a comparison of the results of Example 14 with Example 20 it can be seen that an increase in carbonylation rate can be achieved by the use of both a metal promoter and a heteropolyacid compared to the rate obtainable by the use of a metal promoter alone.

The invention claimed is:

1. A process for the production of acetic acid comprising reacting with carbon monoxide, methanol or a reactive derivative thereof in a liquid reaction composition comprising methyl acetate, a finite concentration of water, acetic acid and a catalyst system, which catalyst system comprises an iridium carbonylation catalyst, methyl iodide co-catalyst, at least one non-hydrohalogenoic acid promoter selected from an oxoacid of the elements of Groups 13 to 17 of the Periodic Table, a superacid, a heteropolyacid and mixtures thereof, in an amount sufficient to provide a promotional effect on the carbonylation rate and optionally at least one of ruthenium, osmium, rhenium, zinc, gallium, tungsten, cadmium, mercury and indium.

2. A process according to claim 1 wherein the non-hydrohalogenoic acid is an oxoacid of the elements of Groups 13 to 17 of the Periodic Table.

3. A process according to claim 2 wherein the oxoacid is selected from $H_2SO_4$, $HNO_3$, $H_3PO_4$ and mixtures thereof.

4. A process according to claim 2 wherein the molar ratio of oxoacid anion to iridium is in the range greater than 0 to 0.4:1.

5. A process according to claim 3 wherein the molar ratio of oxoacid anion to iridium is greater than 0 to 0.35:1.

6. A process according to claim 1 wherein the non-hydrohalogenoic acid is a superacid.

7. A process according to claim 6 wherein the superacid has a non-coordinating anion to iridium.

8. A process according to claim 6 wherein the superacid is a superacid having an anion selected from $BF_4^-$, $PF_6^-$, $(CF_3SO_2)_2N^-$, $CBH_6Br_6^-$, $CF_3SO_3^-$, $SbF_6^-$, $FSO_3^-$ and mixtures thereof.

9. A process according to claim 6 wherein the superacid is selected from $HBF_4$, $HPF_6$, $(CF_3SO_2)_2NH$, $HCBH_6Br_6$ and mixtures thereof.

10. A process according to claim 6 wherein the molar ratio of the superacid anion to iridium is in the range greater than 0 to 2.5:1.

11. A process according to claim 10 wherein the molar ratio of the superacid anion to iridium is in the range greater than 0 to 1:1.

12. A process according to claim 1 wherein the non-hydrohalogenoic acid is a heteropolyacid.

13. A process according to claim 12 wherein the heteropolyacid comprises at least one of molybdenum and tungsten as peripheral atoms.

14. A process according to claim 13 wherein the heteropolyacid is selected from 12-tungstophosphoric acid, 12-molybdophosphoric acid, 12-tungstosilicic acid, 12-molybdosilicic acid and mixtures thereof.

15. A process according to claim 12 wherein the molar ratio of the heteropolyacid anion to indium is in the range greater than 0 to 5:1.

16. A process according to claim 15 wherein the molar ratio of the heteropolyacid anion to iridium is in the range greater than 1 to 4:1.

17. A process according to claim 1 wherein the catalyst comprises at least one of ruthenium, osmium, rhenium, zinc, gallium, tungsten, cadmium, mercury and indium.

18. A process according to claim 17 wherein the catalyst comprises at least one of ruthenium, osmium, rhenium and indium.

19. A process according to claim 1 wherein the concentration of methyl acetate in the liquid reaction composition is in the range 1 to 70% by weight.

20. A process according to claim 19 wherein the methyl acetate concentration is in the range 2 to 50% by weight.

21. A process according to claim 1 wherein the concentration of water in the liquid reaction composition is in the range 1 to 15% by weight.

22. A process according to claim 21 wherein the concentration of water is in the range 1 to 10% by weight.

23. A process according to claim 1 wherein the process is carried out as a continuous process.

* * * * *